United States Patent
Bunke et al.

(10) Patent No.: US 7,703,455 B2
(45) Date of Patent: Apr. 27, 2010

(54) APPARATUS AND METHOD FOR SUPPLYING RESPIRATORY GAS TO A PATIENT IN WHICH RESPIRATORY GAS COMPONENTS ARE METERED WITH GREAT ACCURACY

(75) Inventors: Claus Bunke, Sereetz (DE); Jürgen Manigel, Klingberg (DE); Gerald Panitz, Klenzau (DE); Ralf Dittmann, Lübeck (DE)

(73) Assignee: Dräger Medical AG & Co. KGAA, Lubeck (DE)

( * ) Notice: Subject to any disclaimer, the term of this patent is extended or adjusted under 35 U.S.C. 154(b) by 1215 days.

(21) Appl. No.: 10/926,002

(22) Filed: Aug. 26, 2004

(65) Prior Publication Data

US 2005/0103338 A1    May 19, 2005

(30) Foreign Application Priority Data

Nov. 13, 2003    (DE) ................................. 103 52 981

(51) Int. Cl.
*A61M 15/00*    (2006.01)
(52) U.S. Cl. .............................. 128/204.14; 128/204.22
(58) Field of Classification Search ............ 128/204.21, 128/203.14, 203.16, 204.22, 204.23, 204.25, 128/204.29, 205.23, 205.24, 207.15, 207.16, 128/204.18
See application file for complete search history.

(56) References Cited

U.S. PATENT DOCUMENTS

| 4,637,386 | A |   | 1/1987  | Baum |  |
|-----------|---|---|---------|------|--|
| 4,905,685 | A | * | 3/1990  | Olsson et al. ......... | 128/203.12 |
| 5,094,235 | A | * | 3/1992  | Westenskow et al. .. | 128/204.22 |
| 5,509,406 | A | * | 4/1996  | Kock et al. ............ | 128/203.14 |
| 5,522,381 | A | * | 6/1996  | Olsson et al. ......... | 128/203.12 |
| 5,673,688 | A | * | 10/1997 | Tham et al. ........... | 128/204.22 |
| 5,730,119 | A | * | 3/1998  | Lekholm ............... | 128/200.24 |
| 5,743,253 | A | * | 4/1998  | Castor et al. .......... | 128/200.24 |
| 5,957,129 | A | * | 9/1999  | Tham et al. ........... | 128/204.28 |
| 6,095,137 | A |   | 8/2000  | Wallroth et al. |  |
| 6,131,571 | A | * | 10/2000 | Lampotang et al. .... | 128/204.21 |
| 6,148,816 | A | * | 11/2000 | Heinonen et al. ...... | 128/205.24 |
| 6,260,550 | B1| * | 7/2001  | Weismann et al. ..... | 128/205.24 |
| 6,295,985 | B1| * | 10/2001 | Kock et al. ............ | 128/203.12 |
| 6,349,723 | B1| * | 2/2002  | Kock .................... | 128/203.28 |

(Continued)

FOREIGN PATENT DOCUMENTS

DE    3422066    6/1989

(Continued)

*Primary Examiner*—Danton DeMille
(74) *Attorney, Agent, or Firm*—Nixon & Vanderhye PC

(57) ABSTRACT

An apparatus for supplying respiratory gas to a patient in which respiratory gas components are metered with great accuracy and sources of error are detected early. The apparatus has metering devices for respiratory gas components which are connected, on the leading side of a mixing chamber volume, to a ring line; a first respiratory gas analyzer on the trailing side of the mixing chamber volume; a second respiratory gas analyzer at a patient connection; a regulating device for the respiratory gas components which controls the delivery of respiratory gas components, as a function of the concentration measured with the second respiratory gas analyzer, in such a way that the difference between a predetermined concentration and a measured concentration at the patient connection is minimized; and means for performing a plausibility comparison between the measured values of the first respiratory gas analyzer and the second respiratory gas analyzer.

5 Claims, 1 Drawing Sheet

U.S. PATENT DOCUMENTS

| | | | |
|---|---|---|---|
| 6,520,180 B1 * | 2/2003 | Sahmkow et al. | 128/204.21 |
| 6,553,990 B2 * | 4/2003 | Hoffmann | 128/203.12 |
| 6,679,259 B2 * | 1/2004 | Heesch | 128/204.26 |
| 6,691,705 B2 * | 2/2004 | Dittmann et al. | 128/203.25 |
| 2006/0207593 A1 * | 9/2006 | Dittmann et al. | 128/203.12 |

FOREIGN PATENT DOCUMENTS

| | | |
|---|---|---|
| DE | 4004034 | 11/1990 |
| DE | 100 09 274 | 3/2001 |
| EP | 0 894 506 | 7/1998 |
| EP | 0 983 771 | 3/2000 |
| WO | WO 00/30536 | 6/2000 |

\* cited by examiner

APPARATUS AND METHOD FOR SUPPLYING RESPIRATORY GAS TO A PATIENT IN WHICH RESPIRATORY GAS COMPONENTS ARE METERED WITH GREAT ACCURACY

CROSS REFERENCE TO RELATED APPLICATION

This application is based on and incorporates herein by reference German Patent Application No. DE 103 52 981.0, filed on Nov. 13, 2003.

BACKGROUND OF THE INVENTION

One apparatus for supplying respiratory gas to a patient is known from German Patent DE 34 22 066 C2. In the known ventilator, an inhalation branch and an exhalation branch communicate with one another in the form of a closed ring line. A blower, as a respiratory gas feeder unit, brings about circulation of the respiratory gas in the ring line. For controlling the phases of respiration, a triggerable inhalation valve is included in the inhalation branch and a triggerable exhalation valve is included in the exhalation branch. When the inhalation valve is open and the exhalation valve is closed, the inhalation pressure builds up in the lungs of the ventilated patient. By comparison, when the inhalation valve is closed and the exhalation valve is open, the lungs of the ventilated patient are evacuated via the intake side of the respiratory gas feeder unit. An absorber disposed in a container removes the carbon dioxide contained in the respiratory gas breathed out.

When the known ventilator is used in anesthesiology, a certain quantity of anesthetic agent is admixed with the respiratory gas. In that case, it is important that the predetermined anesthesia concentration at the patient connection be achieved as accurately as possible; that rapid changes of concentration can be attained; and that safety mechanisms are provided that give a warning if incorrect dosages are given.

SUMMARY OF THE INVENTION

It is the object of the invention to disclose an apparatus and a method to enable performing metering of respiratory gas components with great accuracy and detecting sources of error.

This object may be attained with an apparatus for supplying respiratory gas to a patient, including: a ring line with circulation of the respiratory gas; a patient connection communicating with the ring line; a respiratory gas feeder unit for generating a circulation of respiratory gas in the ring line; a mixing chamber volume through which respiratory gas flows; metering devices for respiratory gas components, which are connected on the leading side of the mixing chamber volume to the ring line; a first respiratory gas analyzer on the trailing side of the mixing chamber volume; a second respiratory gas analyzer at the patient connection; a regulating device for the proportion of respiratory gas components in the respiratory gas, which device, as a function of the concentration, measured with one of the respiratory gas analyzers, of respiratory gas components, controls the delivery of respiratory gas components such that the difference between a predetermined concentration and a measured concentration at the patient connection is minimized; and means for performing a plausibility comparison between the measured values of the first respiratory gas analyzer and the second respiratory gas analyzer.

This object may also be attained with A method for supplying respiratory gas to a patient, having an apparatus which has a ring line with circulation of the respiratory gas, a patient connection communicating with the ring line, a respiratory gas feeder unit for generating a respiratory gas circulation in the ring line, and a mixing chamber volume through which the respiratory gas flows, comprising: connecting metering devices for respiratory gas components to the ring line on the leading side of the mixing chamber volume; with a first respiratory gas analyzer, performing a first gas sample analysis on the trailing side of the mixing chamber volume; with a second respiratory gas analyzer, performing a second gas sample analysis at the patient connection; with a regulating device for the proportion of the respiratory gas components in the respiratory gas, as a function of the concentration of respiratory gas components ascertained at the patient connection, controlling the delivery of respiratory gas components in such a way that the difference between the predetermined and the ascertained concentration is minimized; and performing a plausibility comparison between the measured values of the first respiratory gas analyzer and the second respiratory gas analyzer.

An advantage of the invention is essentially that because respiratory gas components are fed separately into the ring line, the regulating circuits for setting a certain concentration of these components in the respiratory gas can operate largely independently of one another. As a result, on the one hand rapid changes of concentration can be attained, and on the other, by feeding the respiratory gas components in upstream of the mixing chamber volume, homogeneous, thorough mixing of the respiratory gas is achieved. This mixing is further reinforced by a blower as a respiratory gas feeder unit, which brings about the circulation of the respiratory gas in the ring line. For regulating and monitoring the proportions of respiratory gas components in the respiratory gas, a first respiratory gas analyzer is provided on the trailing side of the mixing chamber volume, and a second respiratory gas analyzer is provided at the patient connection, as actual-value transducers for the regulation. A regulating device that communicates with both the metering devices and the respiratory gas analyzers controls the delivery of respiratory gas components into the ring line in such a way that the difference between a predetermined concentration and a measured concentration at the patient connection is minimized. Moreover, a plausibility comparison is performed between the measured values of the first respiratory gas analyzer, in the ventilator, and the second respiratory gas analyzer at the patient connection, so that if there are significant deviations, the user is given early warning to enable him to achieve a stable state.

Advantageously, separate metering devices are provided for anesthetic agents and narcosis gas, such as oxygen in combination with laughing gas or air. An anesthesia metering device feeds anesthetic agent vapor into the ring line. A gas mixer creates a mixture of oxygen and laughing gas or of oxygen and air. The regulating device contains separate regulating circuits for the respiratory gas components, anesthetic agent, and oxygen in the ring line.

Advantageously, flow rate meters are provided on the trailing side of the gas mixer and of the anesthesia metering device, for detecting the individual gas flow rates of narcosis gas and anesthetic agent vapor. Taking the measured flow rates of individual gases into account with the flow rate meters makes it possible to perform an additional plausibility comparison with the measured values of the individual gas flow rates and the measured values of the first and second respiratory gas analyzers.

Advantageously, a first reversing valve is provided on the trailing side of the anesthesia metering device and a second reversing valve is provided on the trailing side of the first respiratory gas analyzer. In a first switching position of the reversing valves, the anesthetic agent vapor and the narcosis gas from the gas mixer are fed into the ring line via separate lines on the leading side of the mixing chamber volume, and the anesthesia concentration and the oxygen concentration are measured on the trailing side of the mixing chamber volume. In a second switching position of the reversing valves, conversely, the anesthetic agent vapor is fed into a fresh gas line, which communicates with the gas mixer and leads to the ring line. The measurement of the anesthesia concentration and oxygen concentration is performed directly in the fresh gas line.

The advantage of the second switching position is essentially that the anesthetic agent vapor and the narcosis gas from the gas mixer are united before being fed into the ring line, so that the metering is done regardless of the states in the ring line. By setting a predetermined mixture ratio between anesthetic agent vapor and narcosis gas, a mode of operation without regulation of concentration is possible, in the way that is known from narcosis agent vaporizers operating on the bypass principle. By means of a coupling disposed in the fresh gas line, the possibility exists of disconnecting the fresh gas line from the ring line and using it as a gas supply for an external breathing system.

DESCRIPTION OF THE PREFERRED EMBODIMENT

Figure 1:
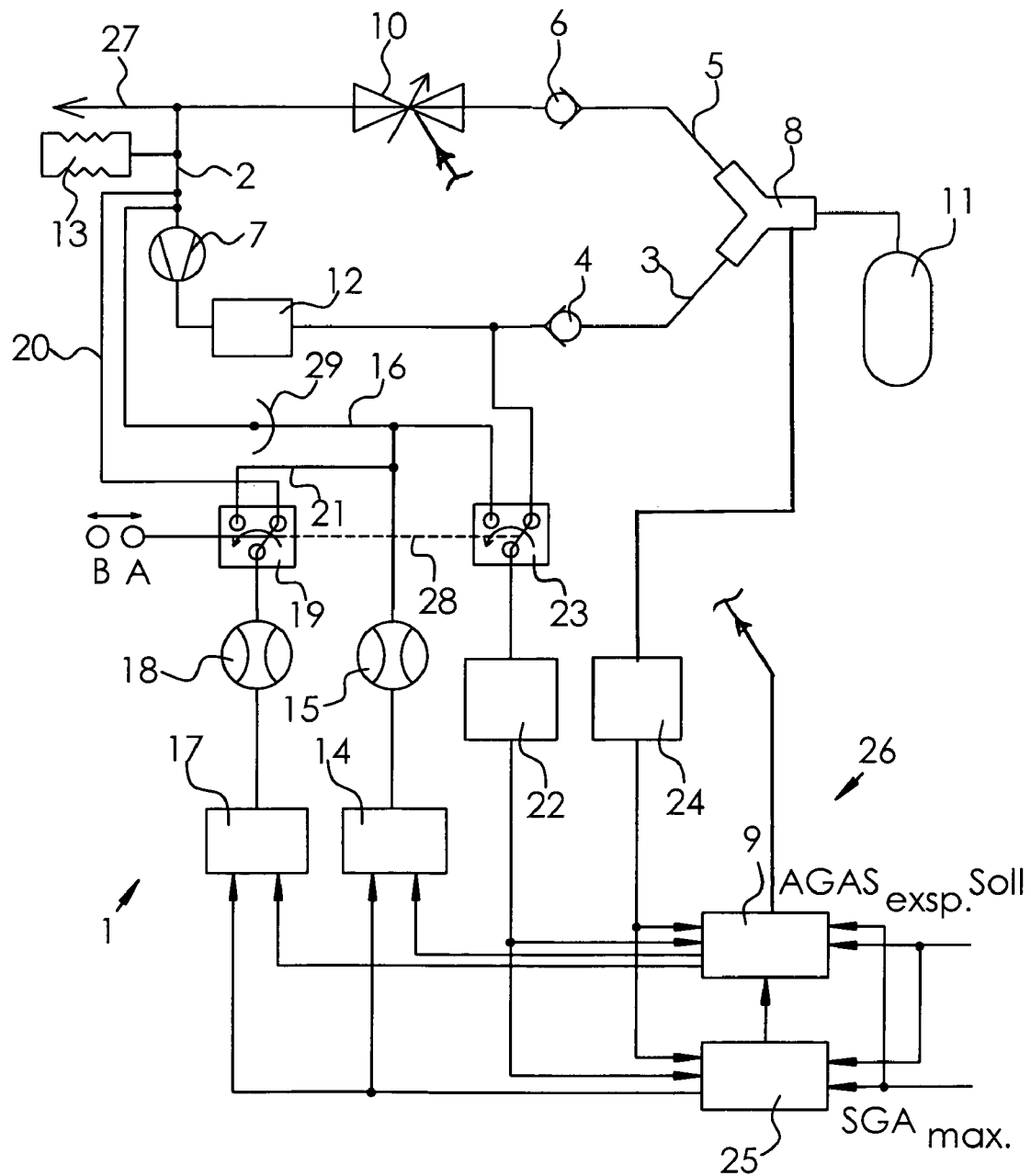
FIG. 1 shows a ventilator apparatus according to an exemplary embodiment of the invention.

FIG. 1 schematically shows a ventilator apparatus 1 with circulation of the breathing air in a ring line 2; the ring line 2 comprises an inhalation branch 3 with an inhalation valve 4 and an exhalation branch 5 with an exhalation valve 6. The respiratory gas is transported in the ring line 2 by a blower 7, as a respiratory gas feeder device, from the inhalation branch 3 into the exhalation branch 5 via a patient connection 8, e.g., mouthpiece or intubation connection. A flow valve 10, disposed in the exhalation branch 5 and triggered by a control unit 9, is closed and opened at the pace of inhalation and exhalation, so that the patient's lungs 11 connected to the patient connection 8 experience a change in respiration pressure. The carbon dioxide given off by the patient's lungs 11 to the exhalation branch 5 is removed with a carbon dioxide absorber 12 disposed on the trailing side of the blower 7. In an alternative embodiment, not shown, the carbon dioxide absorber 12 is located on the leading side of the blower 7. A manual respiration bag 13 connected to the ring line 2 makes manual ventilation possible. The respiratory gas mixture of laughing gas and oxygen required for the ventilation is created in a gas mixer 14 and is fed into the ring line 2 on the leading side of the blower 7 via a first flow rate meter 15 and a fresh gas line 16. Excess respiratory gas can flow out of the ring line 2 during exhalation via an excess-gas outlet 27.

An anesthesia metering device 17 feeds saturated anesthetic agent vapor into the ring line 2 on the leading side of the blower 7 via a second flow rate meter 8, a first reversing valve 19, and a first anesthesia line 20. A second anesthesia line 21, branching off from the first reversing valve, discharges into the fresh gas line 16. The anesthesia concentration in the ring line 2 is measured with a first respiratory gas analyzer 22, which draws the gas sample either from the fresh gas line 16 or from the inhalation branch 3, depending on the switching position, via a second reversing valve 23. A second respiratory gas analyzer 24 performs a measurement of concentration in a gas sample taken from the patient connection 8. The control unit 9 and a monitoring unit 25, which communicate with the respiratory gas analyzers 22, 24 of the anesthesia dosing/metering device 17, with the gas mixer 14 and with the reversing valves 19, 23, together form a regulating device 26 for the anesthesia concentration and oxygen concentration in the ring line 2. For that purpose, the respiratory gas analyzers 22, 24 are embodied such that they can measure both the anesthesia concentration and the oxygen concentration.

The reversing valves 19, 23 communicate with one another via an actuation rod 28 and are actuated in common between the switching positions "A" and "B". In the switching position "A" shown in FIG. 1 of the reversing valves 19, 23, fresh gas and anesthetic agent vapor are fed separately into the ring line 2 via the fresh gas line 16 and the first anesthesia line 20; the gas samples for the respiratory gas analysis are drawn from the inhalation branch 3 by the first respiratory gas analyzer 22. The carbon dioxide absorber 12 serves as a mixing chamber volume for mixing the respiratory gas components.

In switching position "B", conversely, the anesthetic agent vapor is fed directly into the fresh gas line 16, and the gas sample for the first respiratory gas analyzer is drawn from the fresh gas line 16 as well. The switching position "B" is especially suitable for those applications in which the fresh gas line 16 is disconnected at a coupling 29 and connected to an external ventilation system, not shown in the drawing, such as a Kuhn or Bain system.

The respiration apparatus 1 disclosed according to the invention functions as follows:

The actual values of the concentration of the respiratory gas components for the regulating device 26, the oxygen concentration, and the anesthesia concentration are measured with the second respiratory gas analyzer 24; measured values for both inhalation and exhalation are ascertained. In addition, the second respiratory gas analyzer 24 ascertains the carbon dioxide concentration in exhalation.

The first respiratory gas analyzer 22 by comparison serves to monitor oxygen concentration and the anesthesia concentration; depending on the switching position of the reversing valves 19, 23, the concentration of the respiratory gas components is determined in either the inhalation branch 3 or the fresh gas line 16.

For the regulation mode, it must be noted that the respiratory gas analyzers 22, 24 have some measurement uncertainty, which depending on the type of gas can be on the order of magnitude of approximately ±3 vol. %. In the least favorable case, the measurement uncertainty between the measured values of the respiratory gas analyzers 22, 24 is 6 vol. %. In the switching position "A" of the reversing valves 19, 23, the anesthesia concentration is regulated to a measured value for exhalation, and the oxygen concentration is regulated to a measured value for inhalation. In order, in determining the measured value for exhalation for the anesthesia concentration ($AGAS_{exsp.}$) to the measurement uncertainty of a respiratory gas analyzer 22, 24, to limit the tolerance, this measured value is composed of both the measured value in the inhalation branch 3 measured with the first respiratory gas analyzer 22 ($SGA_{insp.}$) and the difference between the measured value for inhalation ($PGA_{insp.}$) and the measured value for exhalation ($PGA_{exsp.}$) of the second respiratory gas analyzer 24, as expressed by the following equation:

$$AGAS_{exsp.} = SGA_{insp.} + (PGA_{exsp.} - PGA_{insp.})$$

In the switching position "B" of the reversing valves 19, 23, regulation is done to the measured value upon inhalation ($AGAS_{insp.}$):

$$AGAS_{insp.} = SGA_{insp.}$$

The oxygen concentration $FO_2$ is regulated to the measured value for inhalation ($SGO_{insp.}$) measured with the first respiratory gas analyzer 22:

$$FO_2 = SGO_{insp.}$$

The measured values ($SGA_{insp.}$) for the anesthesia concentration and ($SGA_{insp.}$) for the oxygen concentration are associated with the first respiratory gas analyzer 22, while the measured values ($PGA_{exsp.}$), ($PGA_{insp.}$) for the anesthesia concentration and ($PGO_{insp.}$) for the oxygen concentration belong to the second respiratory gas analyzer 24.

If, during automatic calibration that is required at regular intervals, one of the respiratory gas analyzers 22, 24 is not ready to perform measurement for a certain period of time, then the corresponding measured value is taken from the other respiratory gas analyzer. A predetermined anesthesia concentration in the respiratory gas upon exhalation is attained by supplying a defined quantity of the anesthetic agent in vapor form to the ring line 2 from the anesthesia metering device 17. For that purpose, a predetermined value for the anesthesia concentration upon inhalation ($SGA_{insp.}$) is calculated by the control unit 9 in such a way that the desired anesthesia concentration upon exhalation ($AGAS_{exsp.}$) is quickly reached and in the steady state matches the set-point predetermination ($AGAS_{exsp.}$.Soll) upon exhalation. At the same time, for the anesthesia concentration upon inhalation ($SGA_{insp.}$), an upper limit value ($SGA_{max.}$) is predetermined in such a way that a maximum anesthesia concentration in the respiratory gas upon inhalation will not be exceeded. The monitoring of the anesthesia gas concentration is performed such that the monitoring unit 25 compares the value ($AGAS_{exsp.}$), measured instantaneously with the first respiratory gas analyzer 22, with the upper limit value ($SGA_{max.}$), and if ($SGA_{max.}$) is reached or exceeded, it generates an alarm signal. In addition, a plausibility comparison is performed between the measured values for the anesthesia concentration and the oxygen concentration of the first respiratory gas analyzer 22 and the second respiratory gas analyzer 24. If the monitoring unit 25 finds significant deviations, a suitable warning is given to the user to allow him to establish a stable operating state of the equipment. The significant deviation is a predetermined percentage of deviation between the measured values of the respiratory gas analyzers 22, 24.

The anesthesia concentration ($SGA_{insp.}$) in the inhalation branch 3, in the steady state, is greater than anesthesia concentration ($AGAS_{exsp.}$) upon exhalation. In the steady state, the compensation for the takeup of anesthetic agent by the patient's lungs 11 is thus assured. If the set-point value for exhalation ($AGAS_{exsp.}$.Soll) increases, the anesthesia concentration in the inhalation branch 3 can be increased for a predetermined length of time via the set-point value for exhalation ($AGAS_{exsp.}$.Soll), so that the target value can be reached as quickly as possible. If the set-point value for exhalation ($AGAS_{exsp.}$.Soll) decreases, the metering of anesthetic agent vapor is discontinued, and the flow rate of fresh gas delivered from the gas mixer 14 is increased, in order to wash excess anesthetic agent out via the excess-gas outlet 27.

In addition to the first respiratory gas analyzer 22, the first flow rate meter 15 on the trailing side of the gas mixer 14 and the second flow rate meter 18 on the trailing side of the anesthesia metering device 17 are provided as monitoring elements. Recourse to these monitoring elements is made if one of the respiratory gas analyzers 22, 24 fails or furnishes implausible measured values.

If in regulated operation an error is found in the monitoring of the anesthesia concentration, then the monitoring unit 25 causes the control unit 9 to switch the reversing valves 19, 23 over to the switching position "B". Simultaneously, the gas flow rate furnished by the gas mixer 14 is increased markedly. As a result of the higher gas flow rate, it is attained that the concentration of the respiratory gas that reaches the patient's lungs 11 will correspond to the values set by the user. This does mean a possible dosage of an overly low anesthesia concentration, but it protects the patient's lungs from excessive dosages of anesthetic agent or an inadequate dosage of oxygen. If no further error is found in the switching position "B" of the reversing valves 19, 23, then a switch back to the switching position "A" is made after a certain period of time. As soon as the respiratory gas analyzers 22, 24 furnish plausible measured values again, the regulating device 26 is activated, and in the regulated mode the respiratory gas concentration is set to the predetermined set-point values for oxygen and anesthetic agent.

What is claimed is:

1. An apparatus for supplying respiratory gas to a patient, including:
    a ring line with circulation of the respiratory gas;
    a patient connection communicating with the ring line;
    a respiratory gas feeder unit comprising a blower for generating a circulation of respiratory gas in the ring line;
    a carbon dioxide absorber through which respiratory gas flows;
    metering devices for respiratory gas components, which are connected to the ring line on a leading side of the carbon dioxide absorber;
    a first respiratory gas analyzer for measuring concentrations of respiratory gas components on a trailing side of the carbon dioxide absorber;
    a second respiratory gas analyzer for measuring concentrations of respiratory gas components at the patient connection;
    a regulating device for the proportion of respiratory gas components in the respiratory gas, said regulating device, as a function of the concentration of respiratory gas components, measured with one of the respiratory gas analyzers, controls the delivery of respiratory gas components such that the difference between a predetermined concentration and a measured concentration at the patient connection is minimized; and
    means for performing a plausibility comparison between measured concentration values of the first respiratory gas analyzer and the second respiratory gas analyzer,
    wherein one of the metering devices is an anesthesia dosing/metering device; and the respective respiratory gas component is anesthetic agent vapor,
    wherein one of the metering devices comprises a gas mixer; and the respective respiratory gas component is oxygen in combination with laughing gas or air,
    wherein the anesthesia dosing/metering device and the gas mixer communicate with the ring line via separate lines, and
    wherein a first flow rate meter is provided on the trailing side of the gas mixer and a second flow rate meter is provided on the trailing side of the anesthesia dosing/metering device; and the plausibility comparison is performed between the measured values of the flow rate meters and the measured values of the first respiratory gas analyzer or the second respiratory gas analyzer.

2. The apparatus of claim 1, wherein a first reversing valve is provided on the trailing side of the anesthesia metering device, and a second reversing valve is provided on the trailing side of the first respiratory gas analyzer; in such a way that in a first switching position "A" of the reversing valves, the metering of the respiratory gas components is effected on the leading side of the mixing chamber volume, and the measurement of the concentration of the respiratory gas components is effected on the trailing side of the mixing chamber volume; and in a second switching position "B", both the metering of anesthetic agent vapor and the metering of the concentration of the respiratory gas components are performed in a fresh gas line leading to the ring line.

3. A method for supplying respiratory gas to a patient, having an apparatus which has a ring line with circulation of the respiratory gas, a patient connection communicating with the ring line, a respiratory gas feeder unit comprising a blower for generating a respiratory gas circulation in the ring line, and a carbon divide absorber through which the respiratory gas flows, comprising:

connecting metering devices for respiratory gas components to the ring line on a leading side of the carbon dioxide absorber;
  with a first respiratory gas analyzer for measuring concentrations of respiratory gas components, performing a first gas sample concentration analysis on a trailing side of the carbon dioxide absorber;
  with a second respiratory gas analyzer for measuring concentrations of respiratory gas components, performing a second gas sample concentration analysis at the patient connection;
  with a regulating device for the proportion of the respiratory gas components in the respiratory gas, as a function of the concentration of respiratory gas components ascertained at the patient connection, that controls the delivery of respiratory gas components in such a way that the difference between the predetermined and the ascertained concentration is minimized; and
  performing a plausibility comparison between measured concentration values of the first respiratory gas analyzer and the second respiratory gas analyzer,
  wherein one of the metering devices is an anesthesia metering device; and the respective respiratory gas component is anesthetic agent vapor,
  wherein one of the metering devices comprises a gas mixer; and the respective respiratory gas component is oxygen in combination with laughing gas or air,
  feeding anesthetic agent vapor and oxygen in combination with laughing gas or air into the ring line via separate lines,
  further comprising:
  on the trailing side of the gas mixer, detecting the gas flow rate with a first flow rate meter;
  on the trailing side of the anesthesia metering device, determining the gas flow rate of anesthetic agent vapor with a second flow rate meter; and
  performing the plausibility comparison between the measured values of the flow rate meters and the measured values of the first respiratory gas analyzer or the second respiratory gas analyzer.

4. The method of claim 3, further comprising:
  providing a first reversing valve on the trailing side of the anesthesia metering device and a second reversing valve on the trailing side of the first respiratory gas analyzer, in such a way that in a first switching position "A" of the reversing valves, the metering of the respiratory gas components is effected on the leading side of the mixing chamber volume and the measurement of the concentration of the respiratory gas components is effected on the trailing side of the mixing chamber volume; and
  in a second switching position "B", performing the metering of anesthetic agent vapor and the measurement of the concentration of the respiratory gas components in a fresh gas line leading to the ring line.

5. An apparatus for supplying respiratory gas to a patient, including:
  a ring line with circulation of the respiratory gas;
  a patient connection communicating with the ring line;
  a respiratory gas feeder unit for generating a circulation of respiratory gas in the ring line;
  a mixing chamber through which respiratory gas flows;
  metering devices for respiratory gas components, which are connected to the ring line on a leading side of the mixing chamber;
  a first respiratory gas analyzer for measuring concentrations of respiratory gas components on a trailing side of the mixing chamber;
  a second respiratory gas analyzer for measuring concentrations of respiratory gas components at the patient connection;
  a regulating device for the proportion of respiratory gas components in the respiratory gas, said regulating device, as a function of the concentration of respiratory gas components, measured with one of the respiratory gas analyzers, controls the delivery of respiratory gas components such that the difference between a predetermined concentration and a measured concentration at the patient connection is minimized; and
  means for performing a plausibility comparison between measured values of the first respiratory gas analyzer and the second respiratory gas analyzer,
  wherein one of the metering devices is an anesthesia dosing/metering device; and the respiratory gas component is anesthetic agent vapor,
  wherein one of the metering devices comprises a gas mixer; and the respiratory gas component is oxygen in combination with laughing gas or air,
  wherein the anesthesia dosing/metering device and the gas mixer communicate with the ring line via separate lines,
  wherein a first flow rate meter is provided on the trailing side of the gas mixer and a second flow rate meter is provided on the trailing side of the anesthesia dosing/metering device; and the plausibility comparison is performed between the measured values of the flow rate meters and the measured values of the first respiratory gas analyzer or the second respiratory gas analyzer, and
  wherein a first reversing valve is provided on the trailing side of the anesthesia metering device, and a second reversing valve is provided on the trailing side of the first respiratory gas analyzer; in such a way that in a first switching position "A" of the reversing valves, the metering of the respiratory gas components is effected on the leading side of the mixing chamber volume, and the measurement of the concentration of the respiratory gas components is effected on the trailing side of the mixing chamber volume; and in a second switching position "B", both the metering of anesthetic agent vapor and the metering of the concentration of the respiratory gas components are performed in a fresh gas line leading to the ring line.

* * * * *